(12) United States Patent
Freeman et al.

(10) Patent No.: US 6,640,132 B1
(45) Date of Patent: Oct. 28, 2003

(54) FORENSIC HYPERSPECTRAL APPARATUS AND METHOD

(75) Inventors: Jenny Freeman, Chestnut Hill, MA (US); Michael J. Hopmeier, Mary Ester, FL (US)

(73) Assignee: Hypermed, Inc., Watertown, MA (US)

( * ) Notice: Subject to any disclaimer, the term of this patent is extended or adjusted under 35 U.S.C. 154(b) by 95 days.

(21) Appl. No.: 09/714,459

(22) Filed: Nov. 17, 2000

Related U.S. Application Data

(60) Provisional application No. 60/165,970, filed on Nov. 17, 1999.

(51) Int. Cl.$^7$ ................................................ A61B 6/00
(52) U.S. Cl. ..................................................... 600/476
(58) Field of Search ................................ 600/476, 775, 600/477, 478, 479, 480, 407, 162; 250/317.1, 337, 345

(56) References Cited

U.S. PATENT DOCUMENTS

| | | | | |
|---|---|---|---|---|
| 5,303,710 A | * | 4/1994 | Bashkansky et al. | 356/301 |
| 5,418,797 A | * | 5/1995 | Bashkansky et al. | 356/301 |
| 5,879,294 A | * | 3/1999 | Anderson et al. | 600/310 |
| 5,998,386 A | * | 12/1999 | Feldman | 514/45 |
| 6,059,724 A | * | 5/2000 | Campell et al. | 128/923 |
| 6,134,010 A | * | 10/2000 | Zavislan | 250/201.3 |
| 6,221,851 B1 | * | 4/2001 | Feldman | 424/93.21 |
| 6,319,189 B1 | * | 11/2001 | Halpern et al. | 600/3 |
| 6,417,797 B1 | * | 7/2002 | Cousins et al. | 342/179 |

* cited by examiner

*Primary Examiner*—Daniel Robinson
(74) *Attorney, Agent, or Firm*—Morrison & Foerster LLP

(57) ABSTRACT

This invention relates to portable imaging devices, such as hyperspectral imaging devices, useful for forensic and other analysis, and methods for using these devices. Devices of the present invention provide images and patterned data arrays representing images in multiple discrete spectra that can then be summed or processed to allow for detection of patterns or anomalies in the data collected.

26 Claims, 1 Drawing Sheet

FORENSIC HYPERSPECTRAL APPARATUS AND METHOD

RELATED APPLICATIONS

The invention described herein claims priority to United States Provisional Patent Application entitled "Forensic Hyperspectral Instrument," Serial No. 60/165,970, filed on Nov. 17, 1999.

BACKGROUND

1. Field of the Invention

This invention relates to imaging devices useful for forensic and other analysis, and to methods for using these devices, and, in particular, to hyperspectral imaging devices that provide images and patterned data arrays representing images in multiple discrete spectra that can then be summed or processed to allow for detection of patterns or anomalies in the data collected.

2. Description of the Background

It is often necessary in investigations (whether they be scientific or criminal) to evaluate an area or environment and identify items or areas of interest. For example, at a crime scene it may be necessary to identify the location of blood or other bodily fluids, shell casings from a gun, individual fibers from clothing or hairs from a body. This is difficult in a complex and complicated environment (i.e., the front of a house, a carpeted room, or a robbery scene). This type of evaluation also is useful in reconstructing events after the fact (i.e., mass killing of hostages in a military setting in connection with a war crimes review, location of people based on evidence as to which way they left an area, reconstruction of natural events such as earthquakes or fires, identification of life or conditions on other planets). Each of these situations shares a similar objective: the need to locate, identify and analyze anomalies or patterns in an image-like data set.

Consequently, there is a need for an instrument that can evaluate a complex scene or environment to provide information as to the characteristics and items in that scene or environment.

SUMMARY OF THE INVENTION

The present invention overcomes the problems and disadvantages associated with current strategies and designs and provides a fast, economical device for analyzing forensic and other evidence in an area of interest, utilizing less equipment and infrastructure/logistics tail than other techniques.

Accordingly, one embodiment of the invention is directed to an apparatus for analyzing a target or target area comprising means for obtaining a data set from the target or target area, and means for providing images and patterned data arrays representing images in multiple discrete spectra that can be summed or processed, singly or in multiples, to allow detection of patterns or anomalies in the data set. Suitable targets include, but are not limited to, geographic locations, biological samples and specimens, structures, textiles, chemicals and man-made materials.

Another embodiment of the invention is directed to a portable hyperspectral imaging apparatus comprising an optical acquisition system; and a diagnostic processor, wherein the diagnostic processor comprises one or more diagnostic modules adapted for forensic analysis. Optionally, the imaging apparatus further comprises an input device, a data storage device, a display, a printer, a communications link, or any combination thereof.

Another embodiment is directed to methods for analyzing a target or target area comprising using instruments according to the present invention to detect patterns or anomalies in a data set obtained from said target or target area.

Other embodiments and advantages of the invention are set forth in part in the description which follows, and in part, will be obvious from this description, or may be learned from the practice of the invention.

DESCRIPTION OF THE INVENTION

Figure 1:
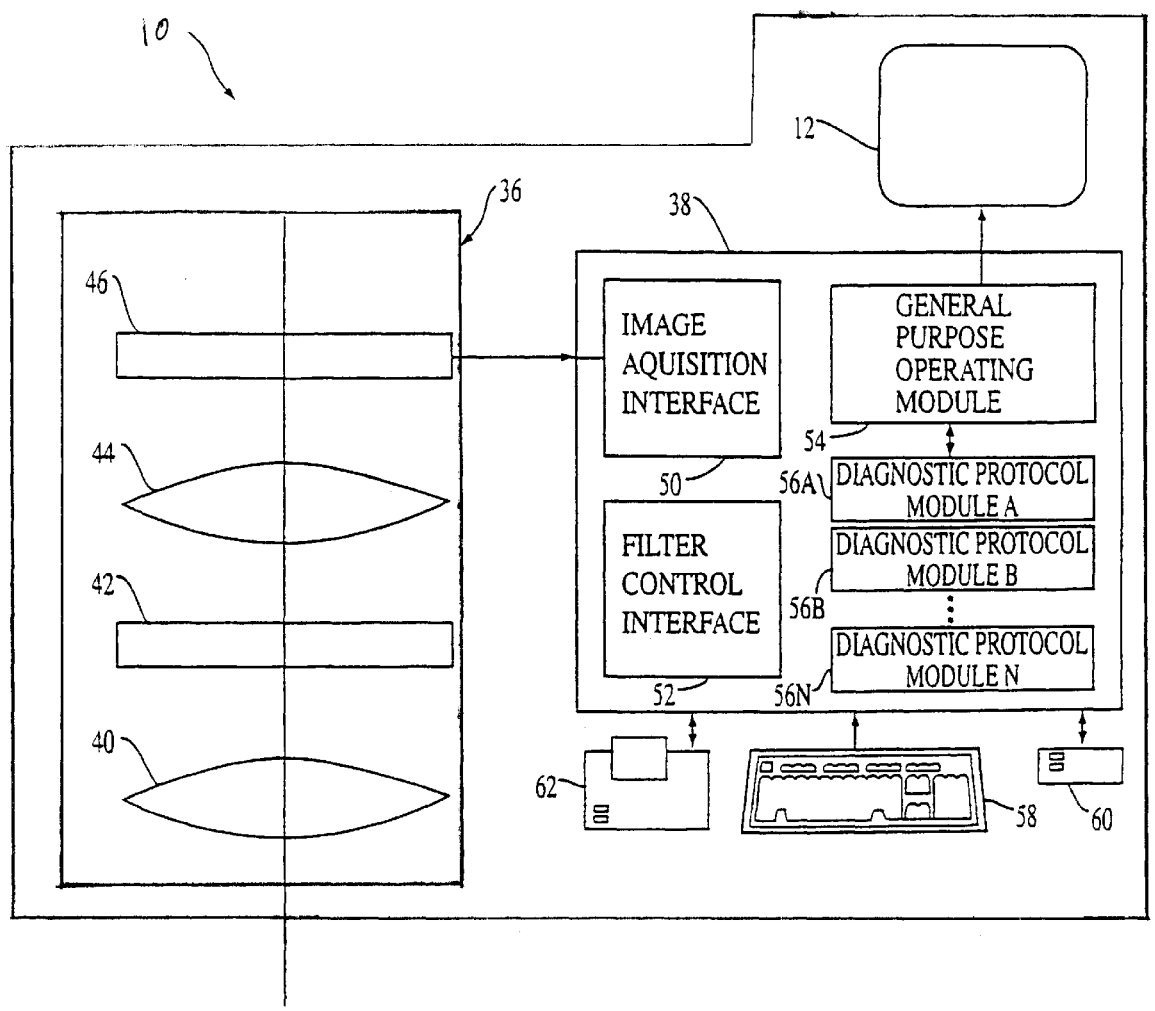
FIG. 1 depicts a portable hyperspectral imaging apparatus.

As embodied and broadly described herein, the present invention is directed to an instrument that provides images and patterned data arrays representing images in multiple discrete spectra that can be summed or processed, either singly or in multiples, providing the ability to detect either patterns or anomalies in a data set. The invention allows the identification of information, areas, objects, and the like that are of interest in a background environment that may be useful in a forensic or criminal investigation. These discrete spectra may be of varying size (different wavelengths or wave numbers) and cover various ranges of the visible, ultra-violet, and infra-red spectra. Further, other image discriminators such as polarization and its phase, as well as intensity under various types of active illumination, can also be used for defining patterns or anomalies.

In addition to having the ability to gather data, the present invention also encompasses the ability to combine the data in various manners including vision fusion, summation, subtraction and other, more complex processes whereby certain unique signatures for information of interest can be defined so that background data and imagery can be removed, thereby highlighting features or information of interest. This can also be combined with automated ways of noting or highlighting items, areas or information of interest in the display of the information.

A portable hyperspectral imaging apparatus according to an embodiment of the invention is depicted in FIG. 1. This embodiment is a portable adaptation of the Inventors' multispectral/hyperspectral instrument disclosed in International Patent Application PCT/US98/22961, filed Oct. 30, 1998, and U.S. patent application Ser. No., 08/961,294, filed on Oct. 30, 1997, which are both incorporated herein by reference. Portable apparatus 10 weighs less than 100 pounds, preferably less than 25 pounds, and more preferably less than 10 pounds. The portable apparatus may be battery operated (not shown) or may have a connector adapted to connect to an existing power source.

Portable apparatus 10 comprises an optical acquisition system 36 and a diagnostic processor 38. Optical acquisition system 36 comprises means to acquire broadband data, visible data, ultraviolet data, infra-red data, hyperspectral data, or any combination thereof. In a preferred embodiment, optical acquiring means comprises a first-stage imaging optic 40, a Liquid Crystal Tunable Filter (LCTF) 42, a second-stage optic 44, and an imaging element 46. Alternatively, optical acquiring means may be any acquisition system suited for acquiring broadband data, visible data, ultraviolet data, infra-red data, hyperspectral data, or any combination thereof.

The first-stage optic receives light collected from a forensic sample and focuses it onto the surface of the LCTF.

LCTF 42 is a programmable filter that filters out all but a wavelength a wavelength region of interest from the light collected from the sample. Second-stage optic 44 receives the remaining light from the LCTF and focuses it onto the image sensor 46. The image sensor is preferably, although not necessarily, a two-dimensional array sensor, such as a charge-coupled device array (CCD), which delivers an image signal to the diagnostic processor 38.

Diagnostic processor 38 includes an image acquisition interface 50, that has an input responsive to an output of the image sensor 46 and an output provided to a general-purpose operating module 54. The general-purpose operating module includes routines that perform image processing, and that operate and control the various parts of the system. It has control output provided to a filter control interface 52, which in turn has an output provided to the LCTF 42. The general-purpose operating module also interacts with a number of diagnostic protocol modules 56A, 56B, ... 54N, and has an output provided to a video display. The diagnostic process includes special purpose hardware, general-purpose hardware with special-purpose software, or a combination of the two. The diagnostic processor also includes an input device 58, which is operatively connected to the general-purpose operating module. A storage device 60 and printer 62 also are operatively connected to the general-purpose operating module.

In operation, portable apparatus is employed near a target, e.g., forensic sample or general area of interest. An operator begins by selecting a diagnostic protocol module using the input device. Each diagnostic protocol module is adapted to detect particular forensic characteristics of the target. In an alternative embodiment, portable apparatus may contain only one diagnostic module adapted for general forensic diagnosis.

Diagnostic processor 38 responds to the operator's input by obtaining a series of transfer functions and an image processing protocol and an image processing protocol from the selected diagnostic protocol module 56. The diagnostic processor provides the filtering transfer functions to the LCTF 42 via its filter control interface 52 and then instructs the image acquisition interface 50 to acquire and store the resulting filtered image from the image sensor 46. The general-purpose operating module 54 repeats these filtering and acquiring steps one or more times, depending on the number of filter transfer functions stored in the selected diagnostic protocol module. The filtering transfer functions can represent bandpass, multiple bandpass, or other filter characteristics.

Once the image acquisition interface 50 has stored images for all of the image planes specified by the diagnostic protocol chosen by the operator, it begins processing these image planes based on the image processing protocol from the selected diagnostic protocol module 56N. Processing operations can include general image processing of combined images, such as comparing the relative amplitude of the collected light at different wavelengths, adding amplitudes of the collected light at different wavelengths, or computing other combinations of signals corresponding to the acquired planes. The computed image is displayed on the display 12. It also can be stored in the storage device 60 or printed out on printer 62.

In an alternative embodiment, diagnostic protocol modules 56, printer 62, display 12, or any combination thereof, maybe be omitted from portable device 10. In this embodiment, acquired images are stored in storage device 60 during operation at a forensic scene. At a later time, these images are transferred via a communications link (not shown) to a second device or computer located at a remote location, for example, forensic laboratory, for analysis. This second device can have the omitted diagnostic protocol modules, printer, display, or any combination thereof. In another embodiment, the stored images are transferred from portable device 10, located at the forensic scene, via a communications link to a remote second device in real time.

Devices of the present invention allow for the creation and unique identification of patterns in data that highlight the information of interest. The data sets in this case may be discrete images, each tightly bounded in spectra, that can then be analyzed. This is analogous to looking at a scene through various colored lenses, each filtering out all but a particular color, and then a recombining these images into something new. Such techniques as false color analysis (assigning new colors to an image that don't represent the true color but are an artifact designed to improve the image analysis by a human) are also applicable. Optionally, optics can be modified to provide a zoom function, or to transition from a micro environment to a macro environment and a macro environment to a micro environment. Further, commercially available features can be added to provide real-time or near real-time functioning. Data analysis can be enhanced by triangulation with two or more optical acquisition systems. Polarizing imagers may be used as desired to enhance signatures for various targets.

It is clear to one skilled in the art that there are many uses for a hyperspectral imager (HSI) according to the invention. The HSI offers the advantages of performing the functions for such uses faster, more economically, and with less equipment and infrastructure/logistics tail than other conventional techniques.

The present invention is useful in a number of diverse applications. In the investigation of crime scene, it is necessary to identify anything that may be considered evidence, either animate or inanimate. To do this, the evidence must be located. Some evidence, such as a body, are easy to locate. Other items of evidence, such as small quantities of bodily fluids or shell casings, are not. The present invention is well-suited to gather this more elusive evidence.

Another related but slightly different application involves accident reconstruction. For example, in a plane crash even the smallest particle or piece of evidence may be crucial to recreating the situation and identifying the cause of the accident.

Another application of the invention relates to investigation of war crimes. For example, it may be necessary to analyze a mass grave associated with possible atrocities committed during war. This may be a very difficult task, particularly if large amounts of time have passed before these investigations can be undertaken. The passage of time between the event and investigation can greatly complicate the identification and evaluation of evidence.

The HSI is capable of not only analyzing for foreign residue on the surface of an object, the HSI can analyze for substances unique for the interaction of that residue with a particular surface. For example, an HSI of the invention can detect the presence of gunpowder, raw or exploded, on tissue surfaces. It also has the ability to detect substances produced by the unique interaction of spent gunpowder with human tissue. In addition, it has the ability to determination the interaction of a foreign body with skin or tissue.

Other applications of the invention relate generally to any type of scientific investigation or analysis. Whether it be the study of large tracts of earth or of other planets from orbiting satellites, or the investigation of the surface of a new material at the microscopic level, hyperspectral analysis using the present invention can be of significant benefit.

Devices according to the present invention are useful for many applications by incorporating diagnostic protocol modules specifically adapted for determining time of death based on change in cellular chemistry analyzed by the imager; evaluating the proximity of a gunshot based on residue left on target; determining the severity of blunt trauma; determining whether oxygen deprivation occurred pre-mortem; evaluating drug status; identifying the location of body fluids on a body or other surface; determining if an injury is old or new; field assessment; location of evidence and evaluation in situ (i.e., brass casings over a large area); determining the location of man made objects; evaluating machined surfaces, which have varying polarization and spectral responses, often differing from those, as a class, found on natural objects; studying bodily fluids over a large area; identifying the point of impact; evaluating an entire scene, rather than sample point by point; identifying different hairs for DNA analysis; locating and separating out of hairs in a carpet; and analyzing chemical residues on suspect (i.e., gun powder pattern will indicate if the gun was fired close to body or with arm outstretched).

By evaluating the patterns associated with deposition of chemical residue, the circumstances of the crime can be determined, e.g., when an arm is bent, the individual's shirt and skin are creased causing a unique pattern of deposition to occur. Devices according to the present invention comprise diagnostic protocol modules adapted for determining timing of event by assessing change of sample over time; assessment of drying out, integrating over time; determination of moisture content; determining velocity of impact based on analysis of tissue and chemical damage; certain species may be separated due to the centrifuge-like environment; analyzing tissue damage/cellular disruption; determining velocity or terminal velocity, or speed of disruption as a result of separation of components due to variations in mass or density (like a centrifuge); analyzing minute particles; identifying the presence of algae feeding on a body in water; concentrations or alterations in the local environment may indicate presence of particular chemicals (i.e., very rich nutrient bed from decomposing body or blood); locating a fluid or other substance by looking for the effect of the particular fluid or substance on grass, concrete or any surface; determining status of structures and near surface phenomena (leaching of minerals from rocks, concrete, roadbeds); and evaluating effects of chemical attacks/processes on materials (i.e., pour a dye on a surface and determine how quickly it is absorbed over an area; determine porosity or other properties of surface).

Other embodiments and uses of the invention will be apparent to those skilled in the art from consideration of the specification and practice of the invention disclosed herein. All references cited herein, including all U.S. and foreign patents and patent applications, are specifically and entirely incorporated by reference. It is intended that the specification and examples be considered exemplary only, with the true scope and spirit of the invention indicated by the following claims.

What is claimed is:

1. A portable apparatus for analyzing a target comprising:
   means for obtaining a data set from a target, and
   means for providing images and patterned data arrays representing images in multiple discrete spectra that can be summed or processed, singly or in multiples wherein said apparatus is adaptable to an application selected from the group consisting of:
   determining time of death based on a change in cellular chemistry of said target; evaluating a proximity of a gunshot based on residue left on said target; determining a severity of blunt trauma; determining whether oxygen deprivation occurred pre-mortem; evaluating drug status; identifying a location of body fluids on a body or other surface; determining if an injury is old or new; field assessment; location of evidence and evaluation in situ; determining the location of man made objects; evaluating machined surfaces, which have varying polarization and spectral responses, often differing from those, as a class, found on natural objects; studying bodily fluids over a large area; identifying a point of impact; evaluating an entire scene, rather than sample point by point; identifying different hairs for DNA analysis; locating and separating out hairs in a carpet; and analyzing chemical residues on a suspect.

2. The apparatus of claim 1 wherein the target is the surface of a tissue.

3. The apparatus of claim 1 wherein said data set is selected from the group consisting of broadband data, ultra-violet data, infra-red data, hyperspectral data, or any combination thereof.

4. A method for analyzing a target comprising using the apparatus of claim 1 to detect patterns or anomalies in a data set obtained from said target.

5. A method for detecting a location of a target comprising using the apparatus of claim 1 to evaluate an area.

6. The method of claim 5 wherein said area is a geographic area.

7. The method of claim 5 wherein said area is a non-living or non-viable area.

8. A method for determining a time an event occurred after death comprising using the apparatus of claim 1 to assess a change in the target.

9. The method of claim 7 wherein said change is determined by comparing said target to a control target.

10. A portable hyperspectral imaging apparatus comprising:
    an optical acquisition system; and
    a diagnostic processor, wherein said diagnostic processor comprises one or more diagnostic modules adapted for forensic analysis wherein said diagnostic protocol module is adaptable to an application selected from the group consisting of:
    determining time of death based on a change in cellular chemistry of said target; evaluating a proximity of a gunshot based on residue left on said target; determining a severity of blunt trauma; determining whether oxygen deprivation occurred pre-mortem; evaluating drug status; identifying a location of body fluids on a body or other surface; determining if an injury is old or new; field assessment; location of evidence and evaluation in situ; determining the location of man made objects; evaluating machined surfaces, which have varying polarization and spectral responses, often differing from those, as a class, found on natural objects; studying bodily fluids over a large area; identifying a point of impact; evaluating an entire scene, rather than sample point by point; identifying different hairs for DNA analysis; locating and separating out hairs in a carpet; and analyzing chemical residues on a suspect.

11. The imaging apparatus of claim 10 further comprising:

an input device;

a data storage device;

a display; and a printer.

12. The imaging of claim 11 further comprising a communications link.

13. The imaging apparatus of claim 10 wherein said optical acquisition system is capable of detecting patterns or anomalies in a data set.

14. A portable apparatus for analyzing a target comprising:

means for obtaining a data set from a target, and means for providing images and patterned data arrays representing images in multiple discrete spectra that can be summed or processed, singly or in multiples wherein said apparatus is adaptable to an application selected from the group consisting of:

determining timing of event by assessing change of sample over time; assessment of drying out, integrating over time; determination of moisture content; determining velocity of impact based on analysis of tissue and chemical damage; certain species may be separated due to the centrifuge-like environment; analyzing tissue damage/cellular disruption; determining velocity or terminal velocity, or speed of disruption as a result of separation of components due to variations in mass or density; analyzing minute particles; identifying the presence of algae feeding on a body in water; concentrations or alterations in the local environment may indicate presence of particular chemicals; locating a fluid or other substance by looking for the effect of the particular fluid or substance on grass, concrete or any surface; determining status of structures and near surface phenomena; and evaluating effects of chemical attacks/processes on materials.

15. The apparatus of claim 14 wherein the target is the surface of a tissue.

16. The apparatus of claim 14 wherein said data set is selected from the group consisting of broadband data, ultraviolet data, infra-red data, hyperspectral data, or any combination thereof.

17. A method for analyzing a target comprising applying the apparatus of claim 14 to detect patterns or anomalies in a data set obtained from said target.

18. A method for detecting a location of a target comprising applying the apparatus of claim 14 to evaluate an area.

19. The method of claim 18 wherein said area is a geographic area.

20. The method of claim 18 wherein said area is a non-living or non-viable area.

21. A method for determining a time an event occurred after death comprising applying the apparatus of claim 14 to assess a change in the target.

22. The method of claim 21 wherein said change is determined by comparing said target to a control target.

23. A portable hyperspectral imaging apparatus comprising:

an optical acquisition system; and a diagnostic processor, wherein said diagnostic processor comprises one or more diagnostic modules adapted for forensic analysis wherein said diagnostic protocol module is adaptable to an application selected from the group consisting of:

determining timing of event by assessing change of sample over time; assessment of drying out, integrating over time; determination of moisture content; determining velocity of impact based on analysis of tissue and chemical damage; certain species may be separated due to the centrifuge-like environment; analyzing tissue damage/cellular disruption; determining velocity or terminal velocity, or speed of disruption as a result of separation of components due to variations in mass or density; analyzing minute particles; identifying the presence of algae feeding on a body in water; concentrations or alterations in the local environment may indicate presence of particular chemicals; locating a fluid or other substance by looking for the effect of the particular fluid or substance on grass, concrete or any surface; determining status of structures and near surface phenomena; and evaluating effects of chemical attacks/processes on materials.

24. The imaging apparatus of claim 23 further comprising:

an input device;

a data storage device;

a display; and a printer.

25. The imaging apparatus of claim 24 further comprising a communications link.

26. The imaging apparatus of claim 23 wherein said optical acquisition system is capable of detecting patterns or anomalies in a data set.

* * * * *